(12) United States Patent
Zhu

(10) Patent No.: US 7,989,623 B2
(45) Date of Patent: Aug. 2, 2011

(54) PROCESS FOR MAKING N-(DIPHENYLMETHYL)PIPERAZINES

(75) Inventor: Jie Zhu, Nijmegen (NL)

(73) Assignee: Synthon BV, Nijmegen (NL)

( * ) Notice: Subject to any disclaimer, the term of this patent is extended or adjusted under 35 U.S.C. 154(b) by 209 days.

(21) Appl. No.: 12/313,614

(22) Filed: Nov. 21, 2008

(65) Prior Publication Data

US 2009/0143582 A1 Jun. 4, 2009

Related U.S. Application Data

(60) Provisional application No. 60/989,528, filed on Nov. 21, 2007, provisional application No. 61/104,124, filed on Oct. 9, 2008.

(51) Int. Cl.
*C07D 241/04* (2006.01)
*C07D 295/00* (2006.01)

(52) U.S. Cl. ..................................... 544/389

(58) Field of Classification Search .................. 544/389
See application file for complete search history.

(56) References Cited

U.S. PATENT DOCUMENTS

| 4,525,358 A | 6/1985 | Baltes et al. |
| 5,478,941 A | 12/1995 | Cossement et al. |
| 5,698,558 A | 12/1997 | Gray |

FOREIGN PATENT DOCUMENTS

| DE | 1139113 | | 11/1962 |
| EP | 617028 | | 9/1994 |
| EP | 955295 | | 11/1999 |
| EP | 1 236 722 A | | 9/2002 |
| GB | 2 076 403 A | | 12/1981 |
| GB | 2 225 321 A | | 5/1990 |
| WO | WO 94/06429 | | 3/1994 |
| WO | WO 2007/066163 | * | 6/2007 |

OTHER PUBLICATIONS

M. Gillard et al., "Binding Characteristics of Cetirizine and Levocetirizine to Human H1 Histamine Receptors: Contribution of Lys191 and Thr194", Molecular Pharmacology 61:391-399, 2002.
G. R. Clemo et al., "The Optical Rotary Powers of Some 4-Substituted Benzhydrylamines" J. Chem. Soc. 1939 pp. 1958-1960.
C. J. Opalka "A Novel Synthesis of the Enantiomers of an Antihistamine Drug by Piperazine Formation from a Primary Amine", Synthesis, Jul. 1995 (7) pp. 766-768.
A. P. Sineokov, et al., Ref.zh.Khim., 1971, Abstr. No. 6Zh476 (Chem. Abstract XP-002464434).
P. Bercot, Compt. Rend. (1964), 258(1), 224-6 (Chem. Abstract XP-002464436).
N. Suciu, Revue Roumaine de Chimie (1966) 11(6), 745-9 (Chem. Abstract XP-002464437).
G. Olah, Acta Chimica Acad. Sci. Hung. (1955), 7, 443-9 (Chem. Abstract XP-002464438).
K. Yoon, Bioorganic and Medicinial Chemistry (2003), 11(15), 3237-3244 (Chem. Abstract XP-002464439).
Chemical Abstracts XP-002464435 (Mar. 28, 2003).

* cited by examiner

*Primary Examiner* — James O Wilson
*Assistant Examiner* — Erich A Leeser
(74) *Attorney, Agent, or Firm* — Muncy, Geissler, Olds & Lowe, PLLC

(57) ABSTRACT

The compound of formula (8), in racemic or single enantiomeric form, is useful in making N-(diphenylmethyl)-piperazines such as cetirizine and levocetrizine.

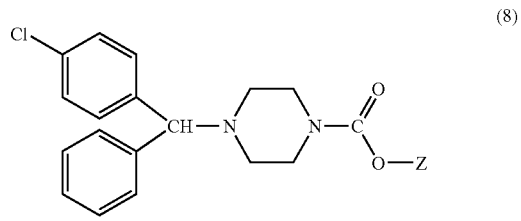

(8)

wherein Z is preferably phenyl.

23 Claims, No Drawings

PROCESS FOR MAKING N-(DIPHENYLMETHYL)PIPERAZINES

This application claims the benefit of priority under 35 U.S.C. §119(e) from U.S. provisional patent application Ser. No. 60/989,528, filed Nov. 21, 2007, and from Ser. No. 61/104,124, filed Oct. 9, 2008; the entire contents of each provisional application being incorporated herein by reference.

BACKGROUND OF THE INVENTION

Cetirizine, chemically 2-[4-[(4-chlorophenyl)-phenyl-methyl]piperazin-1-yl]ethoxy]acetic acid, is a useful pharmaceutical active ingredient. It is an antihistamine whose principal effects are mediated via selective inhibition of $H_1$ receptors. This anti-allergy drug is marketed by the company UCB (which is also the originator of the drug) and/or Pfizer under the brand name Zyrtec®, as a dihydrochloride salt (often referred to as "cetirizine hydrochloride") as shown below.

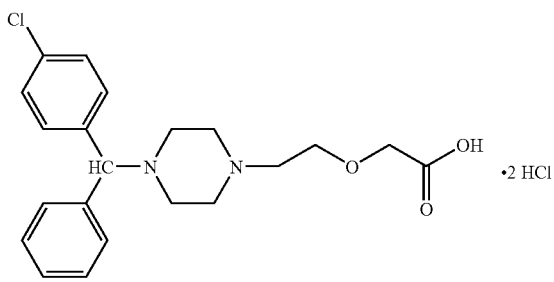

The drug is indicated for the relief of symptoms associated with seasonal allergic rhinitis or perennial allergic rhinitis, as well as for the treatment of the uncomplicated skin manifestations of chronic idiopathic urticaria in adults and children 6 months of age and older.

Cetirizine has one asymmetric carbon, therefore it may be resolved into enantiomers. The pharmaceutically active enantiomer in the racemic cetirizine is the levocetirizine, which is the (R) enantiomer of cetirizine. A medicament comprising levocetirizine was launched in the first quarter of 2001 in Germany followed by a pan-European launch. Levocetirizine is also marketed as the dihydrochloride salt, under the brand name Xyzaal®.

Cetirizine was disclosed in U.S. Pat. No. 4,525,358 (EP 58146). Levocetirizine was specifically disclosed in GB2225321. The method of use of levocetirizine has been disclosed in U.S. Pat. No. 5,698,558 (EP 663828).

Conventionally, levocetirizine may be obtained by resolution of the cetirizine enantiomers as generally suggested, e.g., in WO 94/06429. However, the effectiveness of such process is apparently not high and therefore it is preferred to make levocetirizine from an enantiopure intermediate.

One such useful intermediate is the compound of formula (4)

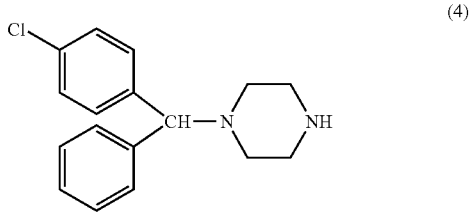

The presence of a quarternary carbon in the formula (4) indicates that the compound may be obtained as a racemate or as a single enantiomer, particularly as the (R) enantiomer. This intermediate may be converted to cetirizine or related analogues, particularly to racemic cetirizine or levocetirizine, by various known processes, e.g., by processes reviewed in U.S. Pat. No. 4,525,358. Resolution of the intermediate (4) into enantiomers by L-tartaric acid as well as the process for making levocetirizine from the corresponding enantiomer of (4) was disclosed in GB2225321. However, the yield and effectiveness of the resolution is insufficient, as shown in U.S. Pat. No. 5,478,941.

The useful starting material for making the compound (4) is the well known and commercially available compound of formula (1),

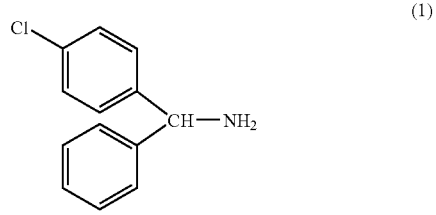

Similarly as the above compound (4), the compound (1) may be obtained as a racemate or as a single enantiomer, particularly as the (R) enantiomer. It is known that the racemic compound (1) can be easily and effectively resolved into enantiomers by a fractional crystallization, preferably by the crystallization of salts with L-tartaric acid. (see U.S. Pat. No. 5,478,941). This makes the compound (1) an important intermediate, particularly in the synthesis of an enantiomerically pure (4).

In a known process for making compound (4) disclosed in EP 617028 (U.S. Pat. No. 5,478,941), the racemic compound of formula (1) and/or its (R)-enantiomer is subjected to a condensation with the N-sulfonated bis-chloroethylamine compound of formula (2),

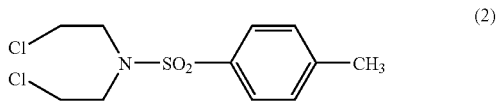

to form the compound of formula (3).

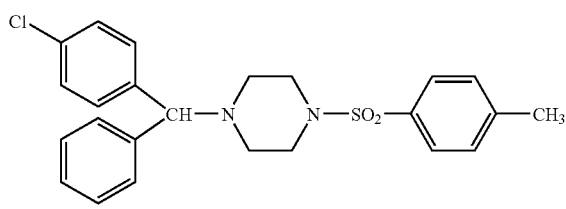

(3)

The compound (3) is then deprotected to form the key intermediate of general formula (4). A disadvantage, however, with the use of the compound of formula (2) in the synthesis of the compound of formula (4) is the need to use a strong deprotecting agent. The tosyl-protective group may be effectively removed only by using a solution of hydrogen bromide in acetic acid. This agent is extremely corrosive, irritating and toxic so that special measures must be used in employing this material.

In principle, one could expect that also an unprotected compound of the formula (5a)

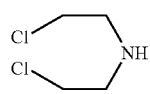

(5a)

might be used for coupling with the compound (1). This would avoid the deprotection step and form the compound (4) directly. But this option is not satisfactory. First, the compound (5a) is an extremely toxic compound ("mustard gas"), and second the reaction is accompanied with a large amount of side products arising particularly from the self-condensation of the compound (5). Thus, the use of an N-protected bis-haloethylamine is clearly preferable. But other potentially useful N-protected compounds, e.g. a carbonyl, alkyl or a triphenylmethyl protecting group, have been reported as unsatisfactory. U.S. Pat. No. 5,478,941 and EP 955295 teach that the above mentioned N-tosyl compound of formula (2) is the only useful compound for the coupling reaction with (1). The protected analogues (a carbonyl, alkyl, or trityl protecting group) caused important racemization of the compound (1) during the coupling reaction and/or the formation of undesired by-products.

Opalka C. J. et al. (Synthesis 1995 (7), p. 766-768) reports that the coupling reaction failed if the amides of formula 6, wherein R represents a carbon-terminated substituent, were used.

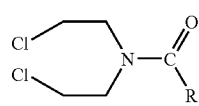

(6)

Thus other protecting groups have proven to be unsuitable so far. It would be desirable to have an alternative process for making the compound of general formula (A), particularly for making the racemate or the R-enantiomer thereof.

SUMMARY OF THE INVENTION

The present invention relates to the discovery of a suitable protecting group and a convenient process for making cetirizine including levocetirizine. Accordingly a first aspect of the invention relates to a process, which comprises:

a) reacting a compound of formula (1) with a compound of formula (7) in the presence of a base,

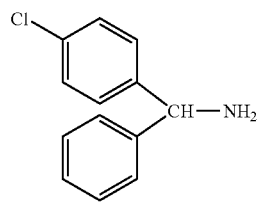

(1)

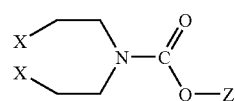

(7)

to form a compound of formula (8):

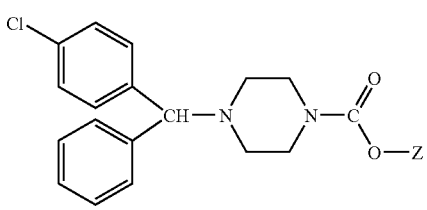

(8)

wherein X is a leaving group reactive with an amine, for instance a halo group such as chloro or bromo group; or a sulphonyl group such as mesyloxy, besyloxy or tosyloxy group; and preferably X is a chloro group;

Z is a C7-C20 aralkyl group or a C6-C20 aryl/alkylaryl group, each of which groups can be substituted by one to four halogen, alkoxy, amino, nitro groups, for instance a phenyl, p-tolyl, p-methoxyphenyl, or benzyl group, and preferably the Z is a phenyl group; and b) deprotecting said compound of formula (8), preferably by an alkaline hydrolysis, to form a compound of formula (4)

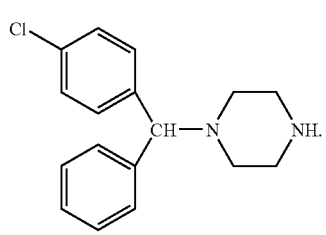

(4)

The compound of formula (4) can be converted to a cetirizine compound. The compounds of formula (1), (8), and (4) can be racemic or substantially a single enantiomer, typically the (R) enantiomer. Each of the above formulas includes salts of the compounds.

Another aspect of the invention relates to the compounds of formula (7), wherein Z is a C7-C20 aralkyl group or a C6-C20 aryl/alkylaryl group, each of which groups can be substituted by one to four alkoxy groups, and of formula (8), wherein Z is a C7-C20 aralkyl group or a C6-C20 aryl/alkylaryl group, each of which groups can be substituted by one to four alkoxy or amino groups. Typically X is chloro and Z is phenyl. The compounds can be racemic or substantially the (R) enantiomer.

A further aspect of the invention relates to a crystalline oxalic acid addition salt of a compound of formula (4). The oxalate allows for isolation of the compound of formula (4) and can be stored.

DETAILED DESCRIPTION OF THE INVENTION

The present invention deals with an alternate process for making the compound of formula (4), which is the key intermediate in the synthesis of pharmaceutically useful compounds including cetirizine compounds. The use of the ester protecting group allows for less stringent deprotection conditions without causing racemization. Thus, the compound of formula (1) can be converted into the compound (4) by a more convenient process without the use of the corrosive, toxic agent of HBr in acetic acid.

As used herein, all chemical formulas having a chiral carbon, e.g., (1), (4), (7), and (8), include both mixtures of the enantiomers such as a racemate as well as substantially a single enantiomer; i.e., at least 90% optical purity, preferably at least 95% optical purity, and including at least 98% and at least 99% optical purity. Similarly, all chemical formulae, e.g., (1) to (8), include the acid addition salts thereof unless explicitly stated to the contrary. For instance, the starting compound (1) may react as a base, or as an acid additions salt, for instance as the hydrochloride.

In the first step of the process of the present invention, the compound of formula (1), a racemate, a single enantiomer thereof or mixtures of any of the preceded, reacts, generally in a liquid phase, with the compound of the general formula (7) to yield the compound of formula (8).

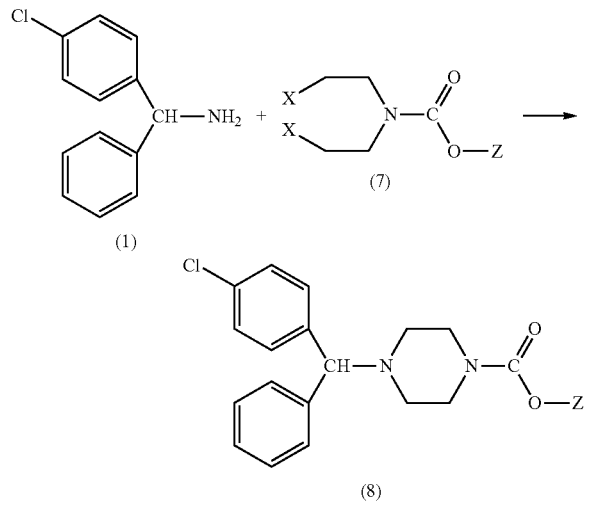

In the formula (7) and (8), Z is a C7-C20 aralkyl group or a C6-C20 aryl/alkylaryl group, each of which can be substituted by one to four halogen, alkoxy, amino, and/or nitro groups. For instance, Z can be a phenyl, p-tolyl, p-methoxyphenyl, or benzyl. Preferably, Z is a phenyl group.

The compound (7) also contains two equal leaving groups X that are reactive with the primary amine in the compound (1) to form the piperazine ring. Such groups X may be represented by a halogen group, or a sulphonyl group such as mesyloxy, besyloxy, anisylsulfonyloxy or tosyloxy group; preferably X is a chloro-group.

While many compound encompassed by general formulas (7) and (8) are novel, some are known per se. For example, compounds of formula (7) in which X=Cl are known, where: Z=CH2CCl3 (WO 2007/066163); Z=p-cresyl, p-chlorophenyl, 2,4-dichlorophenyl, 2,4,6-trichlorophenyl, pentachlorophenyl, p-nitrophenyl, 2-methyl-3,4-dinitrophenyl, p-aminophenyl, or isopropyl (DE 1139113); Z=cyclohexyl (Sineokov, Ref. Zh. Khim. 1971, Abstr. No. 6Zh476); Z=heptyl (Bercot, Compt. Rend. (1964), 258 (1), 224-6); Z=2-(diethylaminoethyl) (Sucio, Revue Roumaine de Chimie, (1966). 11(6), 745-9); Z=2-fluoroethyl (Olah, Acta Chimica Acad. Sci. Hung. (1955), 7, 443-9); and Z=2-aminoethyl (Chem. Abstract XP002464435). Likewise, compounds of formula (8) are known, where: Z=CH2CCl3 (WO 2007/066163); Z=p-nitrophenyl (Yoon, Bioorganic and Medicinal Chemistry (2003), 11(15), 3237-3244); and Z=tert.butyl (EP 1236722).

Accordingly, as compounds per se, the following sub-genuses of compounds (7) and (8) are preferred. For compounds of formula (7), those where Z is a C7-C20 aralkyl group or a C6-C20 aryl/alkyl group, each of which groups can be substituted by one to four alkoxy groups, are contemplated. Most preferred is a compound of formula (7) where X is a chloro and Z is a phenyl. Likewise, for compounds of formula (8), those where Z is a C7-C20 aralkyl group or a C6-C20 aryl/alkyl group, each of which groups can be substituted by one to four alkoxy or amino groups, are contemplated. Most preferred is a compound of formula (8) where Z is a phenyl.

A particularly preferred compound of the general formula (7) for use in the process is N,N-bis(2-chloroethyl)phenyl carbamate of formula (7a),

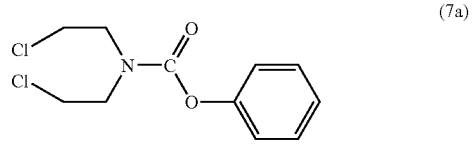

The reaction between compounds (1) and (7) proceeds in the presence of a base, which is preferably an organic base. In a convenient embodiment, a liquid organic base is employed, whereby the liquid organic base serves also as the solvent of the reaction. The preferred liquid organic base is diisopropylethylamine. The reaction preferably proceeds at an enhanced temperature, e.g., at a temperature between 50-150° C., suitably at reflux. Advantageously, potassium iodide may be added as an initiator. The reaction progress may be monitored by a suitable analytical technique, e.g., HPLC. After the reaction, the reaction mixture containing the product (8) may be used for the next step (advantageously, after removal of amine salts formed and/or after removal of at least part of the solvent) or is elaborated to isolate the reaction product (8). In a suitable way of isolation, the reaction mixture is partitioned between an aqueous and organic phase (whereby the organic solvent may be conveniently a hydrocarbon or a chlorinated hydrocarbon) and the product is isolated from the organic phase. The crude product may be purified, if necessary, or may be used in the next step in the crude state. The compound (8) may also be isolated as an acid addition salt.

Dependent on the conformation of the compound (1), the product of formula (8) is a racemate, a single enantiomer thereof or mixtures of any of the preceded. It is an important advantage that the reaction between (1) and (7) proceeds substantially without racemization, so that a substantially single enantiomer of (1) yields the corresponding substantial single enantiomer of (8).

If the preferred compound (7a) is used, the reaction product is the compound of formula (8a), a racemate or a single enantiomer, particularly substantially the (R)-enantiomer, or a mixture of the preceded.

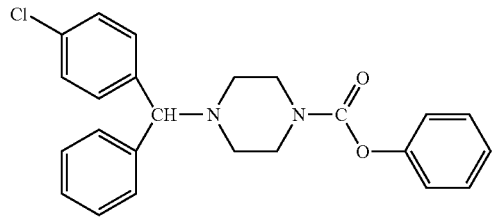

(8a)

In the second step, the compound (8) is subjected to a deprotection step. The N-protective alkoxycarbonyl/aryloxycarbonyl moiety is generally sensitive to alkaline hydrolysis and may be removed by an aqueous alkali, thus avoiding the use of the toxic and irritant HBr/acetic acid agent. The "aqueous alkali" comprises an aqueous solution or suspension of lithium, sodium, potassium or calcium hydroxide or carbonate. The reaction may proceed in the presence of an inert co-solvent, such as in an alcoholic solvent (methanolic, ethanolic, isopropanolic solvent), or the aqueous alkali serves itself as the solvent. The reaction product (4) is then advantageously extracted by a water-insoluble organic solvent, preferably by toluene, and isolated from the organic phase. Side products, if any, may be efficiently removed if the above extraction is done under acidic or alkaline conditions.

Both steps may be also performed in a "one-pot arrangement" as indicated above, i.e., the reaction mixture from the first step is subjected, without an isolation of the intermediate product, to the alkaline hydrolysis by the aqueous alkali.

In an advantageous mode, the formed compound of formula (4), a racemate, a single enantiomer thereof or mixtures of any of the preceded, is isolated from the reaction mixture, and/or purified. For instance, it may be isolated by converting it into an acid addition salt with an organic or inorganic acid that is isolatable as a solid, preferably crystalline, product. An advantageous salt in this respect is the oxalate salt as it may be isolated as a stable crystalline material. The oxalate salt of the compound (4) is a suitable form that allows storage of the compound (4), particularly the racemate or the (R)-enantiomer thereof, for an enhanced period of time. The compound (4) may be however isolated also as a free base, which is preferably a solid product, for instance by a suitable extraction process. In an example, the reaction mixture is partitioned between an organic layer and acidified aqueous layer (in which the product concentrates), the aqueous layer is neutralized, the free base of (4) is extracted by an organic solvent and isolated from this solvent.

The starting (4-chlorophenyl)phenylmethylamine of formula (1) is a known, commercially available compound. It may be used as a racemate or as a single enantiomer, either as a free base or as an acid addition salt, e.g., as the hydrochloride. Both the levorotatory (−)(4-chlorophenyl)phenylmethylamine and the dextrorotatory (+)(4-chlorophenyl)phenylmethylamine may be prepared by the resolution of the racemic compound by (+) or (−) tartaric acid, resp., according to the method described by Clemo et al, J. Chem. Soc. (1939), p. 1958-1960.

The compound of formula (7) may be obtained, for instance, by the condensation of the compound (5)

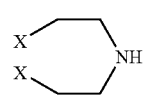

(5)

and/or an acid addition salt thereof, with a chloroformate compound of formula (9)

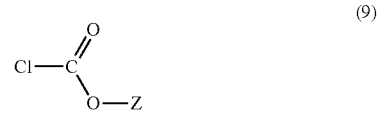

(9)

wherein X and Z have the above meaning. The preferred compound N,N-bis(2-chloroethyl)phenyl carbamate of the formula (7a) is thus obtained by the reaction of the bis(2-chloroethyl)amine of formula (5a) with a phenylchloroformate of formula (9a).

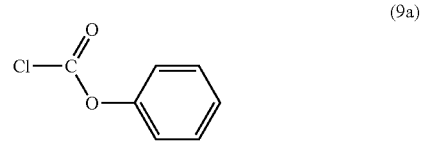

(9a)

The reaction is advantageously performed in an inert solvent, e.g., in a hydrocarbon solvent or a halogenated hydrocarbon solvent, preferably in the presence of a base. The reaction generally proceeds at the ambient or close to ambient temperature (e.g., from 0 to 50 C.). The product is isolated from the reaction mixture by conventional means, e.g., by an extraction into a suitable organic solvent and removal the solvent.

Alternatively, the compounds of formula (7) may be obtained from bis(2-hydroxyethyl) amine and a haloformate (9) according to the scheme

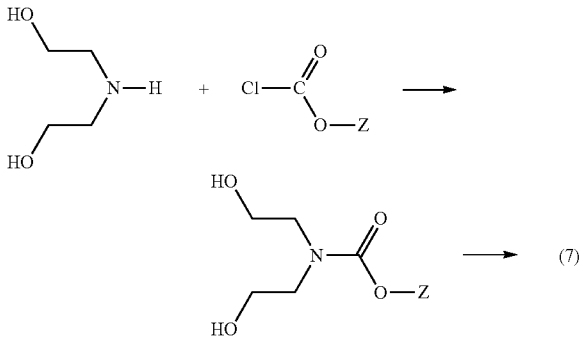

(7)

under general conditions known in the art.

The compound of formula (4), as well as acid addition salts thereof, prepared by the above process, may be converted into a cetirizine compound by known means as described in the above cited patents. As used herein a "cetirizine compound" embraces the cetirizine racemate and its salts as well as substantially one enantiomer (levocetirizine) and salts thereof.

In light of the prior art disclosure, which teaches away of using carbonyl-based N-protecting groups in making the compound of formula (4), the finding of a suitable group of successfully useful carbonyl-comprising compounds for the same purpose is surprising. In particular, the compounds (4) may be obtained by the present process in a high degree of chemical and/or enantiomeric purity, without a danger of racemization and under conditions that are easily and reliably obtainable in an industrial process and avoid using irritating and toxic HBr/acetic acid solution. Consequently, the whole manufacturing process for making pharmaceutically useful compounds cetirizine and/or levocetirizine, if comprising the process of the present invention, becomes more economical and more technically convenient.

The invention is illustrated by the following non-limiting examples.

Example 1

N,N-Bis(2-chloroethyl)phenyl carbamate—Compound of Formula (7a)

To a suspended bis(2-chloroethyl)amine hydrochloride salt (17.85, 0.1 mole) in 200 ml dichloromethane, a 1M NaOH solution (120 ml) was added and stirred at room temperature ("rt") for 1 hour. Separated dichlormethane layer was dried and concentrated in vacuo to give an oily bis(2-chloroethyl)amine free base.

Above crude oil was dissolved in 50 ml dried dichloromethane. With cooling (ice water) and stirring, phenyl chloroformate (12.55 ml, 0.1 mole) was added dropwise. The addition was completed within 20 min followed by addition of triethylamine (22.0 g, 0.22 mole). The mixture was further stirred at room temperature for 2 hours. Water (100 ml) was added, and the mixture was stirred for 20 min. Separated water layer was extracted with dichloromethane (50 ml). Combined dichloromethane layer was washed with water (10 ml), dried and concentrated in vacuo to give an oily product (26.5 g, ~100% yield).

Example 2

N,N-Bis(2-chloroethyl)phenyl carbamate—Compound of Formula (7a)

5 g of Bis(2-chloroethyl)amine HCl was suspended in 30 ml of pre-dried dichloromethane. 4.7 g of phenylchloroformate was added with cooling (ice water) and stirring, while $N_2$ was bubbled through the mixture. The addition was complete within 10 min and was followed by addition of 8.5 ml of triethylamine during 20 minutes.

The mixture was further stirred at ambient temperature for 1 hour:

Then, 10 ml of water was added, and the mixture was stirred for 50 min. till the solid dissolved. The organic layer was separated and washed with 10 ml of HCl 1M and 10 ml of saturated aqueous NaCl. The organic layer was dried and concentrated in vacuo to give an oily product (6.7 g).

Example 3

Step 1—Compound (8a)

A mixture containing (4-chlorophenyl)phenyl methylamine (2.17 g, 10 mmol), N,N-bis(2-chloroethyl)phenyl carbamate [7a] (2.75 g, 10.5 mmol) and diisopropyl ethylamine (5 ml) was stirred ($N_2$ gas was pre-blown through for 1 hour before heating up), with smooth refluxing (130° C. oil bath), for 5 hours.

After cooling down to room temperature, 50 ml dichloromethane and 25 ml water was added, and the mixture was stirred for 20 min. Separated dichloromethane layer was concentrated to give an oil (~4.6 g).

Step 2—Compound (4)

Above oil was dissolved in 20 ml 2-propanol, followed by addition of 5 ml NaOH solution (prepared from 10 g NaOH and 20 ml water). The mixture was stirred, with smooth refluxing (90° C. oil bath), for 2 hours.

The mixture was concentrated in vacuo. 50 ml isopropyl ether and 25 ml water was added, and the mixture was stirred for 30 min. Separated ether layer was washed with water, brine, dried and concentrated to give a crude oily product (2.55 g).

Step 3—Compound (4) oxalate

A solution of above crude product in 25 ml ethyl acetate was stirred at room temperature. Oxalic acid (0.9 g, 10 mmol) was added, the mixture was stirred at rt for 2 hours and further at ~5° C. overnight. Solid was collected by filtration and washed once with ethyl acetate (5 ml). 2.3 g oxalate solid was obtained after drying at 40° C. overnight in vacuo.

Example 4

Compound (4) Oxalate

A mixture containing (4-chlorophenyl)phenyl methylamine (2.17 g, 10 mmol), N,N-bis(2-chloroethyl)phenyl carbamate (2.75 g, 10.5 mmol) and diisopropyl ethylamine (4 ml) was stirred at 90° C. for 1.5 hours ($N_2$ gas was pre-blowed through for 1 hour before heating up), and further with smooth refluxing (13° C. oil bath), for 4 hours.

After cooling down to room temperature, 20 ml 2-propanol was added followed by addition of 3 ml NaOH solution (prepared from 10 g NaOH and 10 ml water). The mixture was stirred, with smooth refluxing (90° C. oil bath), for 2 hours.

After cooling down to rt, solid was filtered off via a celite layer and washed with toluene (75 ml).

The filtrate and washings were combined and partly concentrated in vacuo to get rid of most 2-propanol. Then it was washed with NaOH (1M, 15 ml) and brine, and dried.

With stirring at rt, a solution of oxalic acid (0.9 g, 10 mmol) in ethanol (1 ml) was added, the mixture was stirred at rt for 2 hours and further at ~5° C. overnight. Solid was collected by filtration and washed once with ethyl acetate (5 ml). 2.35 g oxalate solid was obtained after drying at 40° C. overnight in vacuo.

Example 5

Compound (4)

Step 1—Compound (8a)

A mixture containing (4-chlorophenyl)phenyl methylamine hydrochloride salt (5.05 g, 20 mmol), N,N-bis(2-chloroethyl)phenyl carbamate (5.76 g, 22 mmol) and diisopropyl ethylamine (12 ml) was stirred at 80° C. for 2 hours ($N_2$ gas was blown through during the reaction), and further at 100° C. for 9 hours.

After cooling down to 50° C., 20 ml ethyl acetate was added. Mixture was stirred for 20 Min, while the temperature further went down to rt. Solid was filtered off and washed with Ethyl acetate (2×5 ml). Filtrate and washings were combined, and 50 ml ethyl acetate was added. The ethyl acetate solution was washed with $H_2O$ (50 ml), NaOH (1M, 2×50 ml), $H_2O$ (20 ml), brine (20 ml), dried and concentrated to give an oily material (8:8 g).

Step 2—Compound (4)

Above crude material was dissolved in a solution containing NaOH (4 g) in 10 ml $H_2O$ and 40 ml 2-propanol. With stirring, mixture was refluxed for 3 hours.

The mixture was concentrated in vacuo to get rid of 2-propanol and redissolved in 100 ml ethyl acetate and 100 ml $H_2O$. The mixture was stirred for 20 min, and layers were separated. 20 ml HCl (2M) was added to the ethyl acetate layer and stirred for 20 min. Separated acid layer was basified. The mixture was extracted with ethyl acetate (2×50 ml). Combined ethyl acetate layer was washed with $H_2O$ (10 ml), brine (10 ml), dried and concentrated in vacuo to give the desired product (2.5 g), which was solidified while seeded.

Example 6

Compound (8a)

A mixture containing (4-chlorophenyl)phenyl methylamine hydrochloride (2.53 g, 10 mmol), N,N-bis(2-chloroethyl)phenyl carbamate (2.88 g, 11 mmol) and diisopropyl ethylamine (5 ml) was stirred ($N_2$ gas was pre-blown through for 1 hour before heating up), with smooth refluxing (130° C. oil bath), for 6 hours.

After cooling down to room temperature, 50 ml ethyl acetate and 25 ml water was added. Mixture was stirred for 10 min and solid was filtered off. The filtrate was washed with HCl (1M, 15 ml), $H_2O$ (15 ml), brine (15 ml), dried and concentrated to give a crude product (4.4 g).

The crude product was purified by chromatography (2% to 10% ethyl acetate in heptane were used as eluents). After removal of the solvent, the purified product solidified at rt (2.8 g). Analytical sample was obtained by washing of the solid with heptane.

$^1$H NMR (400 MHz, $CDCl_3$):

δ 7.40-7.05 (m, 14H, Ph-H), 4.27 (s, 1H, CH-piperazine), 3.7-3.5 (br, 4H, piperazine-H), 2.43 (m, 4H, $\overline{\text{piperazine}}$-H).

EI/MS: 407 ($M^+$+1), 201 ($M^+$-N($CH_2CH_2$)$_2$COOPh).

Example 7

Compound (4)—R Enantiomer

Step 1—Compound (8a)—R Enantiomer

A mixture containing (R)-(4-chlorophenyl)phenyl methylamine free base (4.34 g, 20 mmol, optical purity 99%), N,N-bis(2-chloroethyl)phenyl carbamate (5.76 g, 22 mmol) and diisopropyl ethylamine (10 ml) was stirred under nitrogen at 90° C. for 1 hour and further at 115° C. for 5 hours.

After cooling down, 20 ml ethyl acetate was added. Mixture was stirred for 20 min, solid was filtered off and washed with ethyl acetate (2×25 ml). Filtrate and washings were combined, washed with $H_2O$ (2×25 ml), and concentrated to give an oily material (8.9 g).

Step 2—Compound (4)—R Enantiomer

Above crude material was dissolved in a solution containing 4 g NaOH in 10 ml $H_2O$ and 40 ml 2-propanol. With stirring, mixture was refluxed for 3 hours.

The mixture was concentrated in vacuo to get rid of 2-propanol and redissolved in 50 ml ethyl acetate and 20 ml $H_2O$. The mixture was stirred for 20 min, and layers were separated. 20 ml HCl (2M) was added to the ethyl acetate layer and stirred for 20 min. Separated ethyl acetate layer was extracted again with 10 ml HCl (1M). Acidic layers were combined and basified. The mixture was extracted with ethyl acetate (2×50 ml). Combined ethyl acetate layer was washed with $H_2O$ (10 ml), brine (10 ml), dried and concentrated in vacuo to give the desired product (2.7 g), which was solidified while seeded. Optical purity ~99%.

Example 8

Compound (4)—R Enantiomer

Step 1

A mixture containing 10.05 g (R)-(4-Cl-phenyl)phenyl methylamine, 13.34 g N,N-bis(2-chloroethyl)phenyl carbamate, 4.2 g potassium iodide and 25 ml diisopropyl ethylamine was stirred at 115° C. (oil bath: 140° C.) for 3 h 30 min. While cooling down, 180 ml dichloromethane was added, and the mixture was stirred for 20 min. Then, HCl (6M) was added until pH was ~5. The organic layer was separated, washed with 10 ml aqueous NaCl, dried over $Na_2SO_4$ and concentrated at reduced pressure Step 2

Above crude material was mixed with 100 ml 2-propanol, 25 ml water and 13.5 g sodium hydroxide. The mixture was refluxed for 3.5 hours. It was concentrated in vacuo to get rid of 2-propanol and re-dissolved in a mixture of 100 ml toluene and 40 ml water. The mixture was stirred for 45 min. The solid was filtered off. The organic layer was separated and washed with 10 ml water, and extracted twice with 50 ml HCl (2M). After washing the aqueous layer with 25 ml toluene, the mixture was basified to pH 8-9, extracted with 100 ml toluene. The organic layer was washed with 10 ml water, dried and concentrated in vacuo to give the desired product (8 g, ~60% yield). Stirring the crude product in 20 ml of toluene for 20 minutes, followed by filtrating and drying at 40° C. (vacuum oven) overnight, gave 4.5 g of the purified product.

Example 9

N,N-Bis(2-chloroethyl)p-tolyl carbamate

To a suspension of bis(2-chloroethyl)amine hydrochloride salt (5.23 g, 0.03 mole) in 45 ml dry dichloro-methane, with cooling (ice water) and stirring, p-tolyl chloroformate (5 g, 0.03 mole) was added dropwise. The addition was complete within 20 min and was followed by addition of triethylamine (6.46 g, 0.06 mole) during 45 min. The mixture was further stirred at room temperature for 1 hour. Water (12 ml) was added, and the mixture was stirred for 10 min. Separated dichchloromethane layer was washed with HCl 1M (12 ml), brine (10 ml), dried and concentrated in vacuo to give an oily product (6.67 g, ~80.5% yield).

Example 10

Compound (4) Oxalate—R-Enantiomer

A mixture containing (4-chlorophenyl)phenyl methylamine free base (1.05 g, 4.8 mmol), N,N-bis(2-chloroethyl) p-tolyl carbamate (1.39 g, 5 mmol) potassium iodide (0.42 g, 2.5 mmol) and diisopropyl ethylamine (2.6 ml) was stirred at 120° C. (oil bath 135° C.) for 5 hours. While cooling down 7 ml ethyl acetate was added. The mixture was stirred at ambient temperature overnight. The solid was filtered off and washed with ethyl acetate (5 ml) and concentrated to give an oily material (2.64 g).

Above crude material was dissolved in a solution containing 1.3 g NaOH in 2.5 ml H$_2$O and 10 ml 2-propanol. The mixture was refluxed for 1 hour 30 min.

The mixture was concentrated in vacuo to get rid of 2-propanol and redissolved in 10 ml toluene and 5 ml H$_2$O. The mixture was stirred for 30 min. The solid was filtered off and layers were separated. 10 ml HCl (2M) was added to the toluene layer and stirred for 20 min. The separated toluene layer was extracted again with 10 ml HCl (1M). The acidic layers were combined, washed with 10 ml toluene and basified. The mixture was extracted with toluene (15 ml). The separated organic layer was washed with H$_2$O (10 ml), dried and concentrated in vacuo to give the desired product (840 mg oil).

To the crude product ethyl acetate (25 ml) was added, followed by addition of 0.9 g oxalic acid dissolved in 2 ml EtOH. The suspension was stirred 4 h at ambient temperature and overnight at 5° C. Solid obtained was filtered off and dried at 30° C. under vacuum to give a white solid material (1 g, 53% yield, 98.96% ee purity).

Example 11

N,N-bis(2-chloroethyl)p-methoxyphenyl carbamate

To a suspension of bis(2-chloroethyl)amine hydrochloride salt (4.78 g, 0.026 mole) in 45 ml dry dichloro-methane, with cooling (ice water) and stirring, 4-methoxyphenyl chloroformate (5 g, 0.026 mole) was added dropwise. The addition was complete within 20 min. and was followed by addition of triethylamine (5.95 g, 0.05 mole) during 55 min. The mixture was further stirred at room temperature for 1 hour. Water (12 ml) was added, and the mixture was stirred for 10 min. Separated dichchloromethane layer was washed with HCl 1M (12 ml), brine (10 ml), dried and concentrated in vacuo to give an oily product (7 g, ~89.7% yield).

Example 12

Compound (4) Oxalate—R-Enantiomer

A mixture containing (4-chlorophenyl)phenyl methylamine free base (1.05 g, 4.8 mmol), N,N-bis(2-chloroethyl) 4-methoxy phenyl carbamate (1.49 g, 5 mmol) potassium iodide (0.42 g, 2.5 mmol) and diisopropyl ethylamine (2.6 ml) was stirred at 120° C. (oil bath: 135° C.) for 5 hours.

While cooling down, 7 ml ethyl acetate was added. Mixture was stirred at ambient temperature overnight. The solid was filtered off and washed with ethyl acetate (5 ml) and concentrated to give an oily material (2.734 g).

Above crude material was dissolved in a solution containing 1.3 g NaOH in 2.5 ml H$_2$O and 10 ml 2-propanol. The mixture was refluxed for 2 hour 45 min.

The mixture was concentrated in vacuo to get rid of 2-propanol and redissolved in 10 ml toluene and 5 ml H$_2$O. The mixture was stirred for 30 min. The solid was filtered off and layers were separated. 10 ml HCl (2M) was added to the toluene layer and was stirred for 20 min. Separated toluene layer was extracted again with 10 ml HCl (1M). Acidic layers were combined, washed with 10 ml toluene and basified. The mixture was extracted with toluene (15 ml). The separated organic layer was washed with H$_2$O (10 ml), dried and concentrated in vacuo to give the desired product (800 mg oil). To the crude product ethyl acetate (25 ml) was added followed by addition of 0.9 g oxalic acid dissolved in 2 ml EtOH. The suspension was stirred 4 h at ambient temperature and overnight at 5° C. The solid obtained was filtered off and dried at 40° C. under vacuum to give a solid material (0.86 g, 45.7% yield, 98.77% ee purity).

Example 13

N,N-Bis(2-chloroethyl)p-nitrophenyl carbamate

To a suspension of bis(2-chloroethyl)amine hydrochloride salt (4 g, 0.022 mole) in 25 ml dry dichloro-methane, with cooling (ice water) and stirring, 4-nitrophenylchloroformate (4.6 g, 0.022 mole) was added dropwise. The addition was complete within 10 min and was followed by addition of triethylamine (5 g, 0.049 mole) during 1 hour. The mixture was further stirred at room temperature for 1 hour. Water (10 ml) was added, and the mixture was stirred for 10 min. Separated dichchloromethane layer was washed with HCl 1M (10 ml), brine (10 ml), dried and concentrated in vacuo to give an oily product (6.4 g, ~94.8% yield).

Example 14

Compound (4) Oxalate—R-Enantiomer

A mixture containing (4-chlorophenyl)phenyl methylamine free base (4.1 g, 18.8 mmol), N,N-bis(2-chloroethyl) 4-nitrophenyl carbamate (6.4 g, 20.8 mmol) potassium iodide (1.7 g, 10 mmol) and diisopropyl ethylamine (10.2 ml) was stirred at 140° C. (oil bath) for 4 hours.

While cooling down, 60 ml dichloromethane was added. The mixture was stirred at ambient temperature for 20 min. 30 ml HCl (1M) was added to the dichloromethane. The organic layer was separated washed with NaCl (5 ml) dried and concentrated to give an oily material (13.6 g).

Above crude material was dissolved in a solution containing 5.3 g NaOH in 10 ml H$_2$O and 42 ml 2-propanol. The mixture was heated til 50° C. for 3 h 30 min.

The mixture was concentrated in vacuo to get rid of 2-propanol and redissolved in 40 ml toluene and 20 ml H$_2$O. The mixture was stirred for 30 min, the solid was filtered off and layers were separated. 40 ml HCl (2M) was added to the toluene layer and stirred for 20 min. Separated toluene layer was extracted again with 40 ml HCl (1M). Acidic layers were combined, washed with 40 ml toluene and basified. The mixture was extracted with toluene (80 ml). The separated organic layer was washed with H$_2$O (10 ml), NaCl (10 ml) dried and concentrated in vacuo to give the desired product (1.2 g oil). To the crude product ethyl acetate (25 ml) was added, followed by addition of 0.9 g oxalic acid dissolved in 2 ml EtOH. Suspension was stirred 4 h at ambient temperature and overweekend at 5° C. Solid obtained was filtered off and dried at air to give a solid material (1.3 g, 17.6% yield). 98.56% ee purity.

Example 15

Bis (2-chloroethyl)2,2,2-trichloroethyl carbamate

To a suspension of bis(2-chloroethyl)amine hydrochloride salt (5 g, 0.028 mole) in 30 ml dry dichloro-methane, with cooling (ice water) and stirring, 2,2,2-Trichloroethyl chloroformate (6.5 g, 0.03 mole) was added dropwise. The addition was complete within 20 min and was followed by addition of triethylamine (6.46 g, 0.063 mole) during 50 min. The mixture was further stirred at room temperature for 1 hour. Water (10 ml) was added, and the mixture was stirred for 15 min. Separated dichchloromethane layer was washed with HCl 1M (10 ml), brine (10 ml), dried and concentrated in vacuo to give an oily product (8.81 g, ~100% yield).

Example 16

Compound (4) Oxalate—R-Enantiomer

A mixture containing (4-chlorophenyl)phenyl methylamine free base (4.1 g, 18.8 mmol), N,N-bis(2-chloroethyl) 2,2,2-Trichloroethyl carbamate (6.59 g, 20 mmol), potassium iodide (1.7 g, 10 mmol) and diisopropyl ethylamine (10 ml) was stirred at 140° C. (oil bath) for 4 hours 20 min.

While cooling down, 60 ml dichloromethane was added. The mixture was stirred at ambient temperature for 20 min. 35 ml HCl (1M) was added to the dichloromethane. The organic layer was separated washed with NaCl (10 ml) dried and concentrated to give an oily material (11.1 g).

Above crude material was dissolved in a solution containing 5.3 g NaOH in 10 ml $H_2O$ and 45 ml 2-propanol. The mixture was heated til 50° C. for 4 h.

The temperature was increased til 70° C. and was stirred for 2 hours, then overnight at ambient temperature, 2 h at 70° C., 2 h at 100° C. Then, 2.5 g NaOH were added and was stirred 2 h more at 100° C. and overnight at ambient temperature. The mixture was concentrated in vacuo to get rid of 2-propanol and redissolved in 40 ml toluene and 20 ml $H_2O$. The mixture was stirred for 15 min, the solid was filtered off and layers were separated. 25 ml HCl (2M) was added to the toluene layer and stirred for 20 min. Separated toluene layer was extracted again with 25 ml HCl (2M). Acidic layers were combined, washed with 20 ml toluene and basified. The mixture was extracted with toluene (80 ml). The separated organic layer was washed with $H_2O$ (10 ml), dried and concentrated in vacuo to give the desired product. To the crude product ethyl acetate (25 ml) was added followed by addition of 1.7 g oxalic acid dissolved in 2 ml EtOH. Suspension was stirred 4 h at ambient temperature and overnight at 5° C. Solid obtained was filtered off and dried at air to give a solid material (1.2 g, 16.2% yield). 98.64% ee purity Example 17

N,N-Bis(2-chloroethyl)isobutyl carbamate

To a suspension of bis(2-chloroethyl)amine HCl salt (5 g, 0.028 mole) in 30 ml dry dichloro-methane, with cooling (ice water) and stirring, isobutyl chloroformate (4.13 g, 0.03 mole) was added dropwise. The addition was complete within 10 min and was followed by addition of triethylamine (6.46 g, 0.063 mole) during 1 h. The mixture was further stirred at room temperature for 1 hour. Water (10 ml) was added, and the mixture was stirred for 15 min. Separated dichchloromethane layer was washed with HCl 1M (10 ml), brine (10 ml), dried and concentrated in vacuo to give an oily product (6.35 g, ~93.7% yield).

Example 18

Compound (4) Oxalate—R-Enantiomer

A mixture containing (4-chlorophenyl)phenyl methylamine free base (4.1 g, 18.8 mmol), N,N-bis(2-chloroethyl) 4-nitrophenyl carbamate (5 g, 20.7 mmol) potassium iodide (1.7 g, 10 mmol) and diisopropyl ethylamine (10 ml) was stirred at 140° C. (oil bath), for 5 hours 30 minutes.

While cooling down, 60 ml dichloromethane was added. The mixture was stirred at ambient temperature for 20 min. 35 ml HCl (1M) was added to the dichloromethane. The organic layer was separated washed with NaCl (10 ml) dried and concentrated to give an oily material (10.4 g).

Above crude material was dissolved in a solution containing 5.6 g NaOH in 10 ml $H_2O$ and 45 ml 2-propanol. The mixture was heated til 90° C. for 24 hours. 5 grams more of NaOH were added and was stirred for 24 hours.

The mixture was concentrated in vacuo to get rid of 2-propanol and redissolved in 40 ml toluene and 20 ml $H_2O$. The mixture was stirred for 15 min, solid was filtered off and layers were separated. 40 ml HCl (2M) was added to the toluene layer and stirred for 20 min. Separated toluene layer was extracted again with 40 ml HCl (1M). Acidic layers were combined, washed with 40 ml toluene and basified. The mixture was extracted with toluene (80 ml). The separated organic layer was washed with $H_2O$ (10 ml), NaCl (10 ml) dried and concentrated in vacuo to give the desired product. To the crude product in ethyl acetate (25 ml) was added followed by addition of 1.7 g oxalic acid dissolved in 2 ml EtOH. Suspension was stirred 4 h at ambient temperature and overweekend at 5° C. Solid obtained was filtered off, stirred again o/n in 10 ml EtOH, filtered off and dried at air to obtain 500 mg solid (11% yield)

Example 19

N,N-Bis(2-chloroethyl)benzyl carbamate

To a suspension of bis(2-chloroethyl)amine hydrochloride salt (5 g, 0.028 mole) in 30 ml dry dichloro-methane, with cooling (ice water) and stirring, benzyl chloroformate (5.1 g, 0.03 mole) was added dropwise. The addition was complete within 10 min and was followed by addition of triethylamine (6.46 g, 0.063 mole) during 1 h. The mixture was further stirred at room temperature for 1 hour. Water (10 ml) was added, and the mixture was stirred for 15 min. Separated dichchloromethane layer was washed with HCl 1M (10 ml), brine (10 ml), dried and concentrated in vacuo to give an oily product (7 g, ~95.5% yield, 80% pur).

Example 20

Compound (4) Oxalate—R-Enantiomer

A mixture containing (4-chlorophenyl)phenyl methylamine free base (4.1 g, 18.8 mmol), N,N-bis(2-chloroethyl) benzyl carbamate (7 g, 26.7 mmol) potassium iodide (1.7 g, 10 mmol) and diisopropyl ethylamine (10 ml) was stirred at 135° C. (oil bath), for 4 hours.

While cooling down, 60 ml dichloromethane was added. The mixture was stirred at ambient temperature for 20 min. 35 ml HCl (1M) was added to the dichloromethane. The organic layer was separated, washed with NaCl (10 ml) dried and concentrated to give an oily material (10 g). The impure material was purified with AcOEt/heptane column (3→50%).

0.5 grams of above pure material was dissolved in a solution containing 1.3 g NaOH in 1.2 ml $H_2O$ and 5 ml 2-propanol. The mixture was heated til 100° C. for 5 h. The mixture was concentrated in vacuo to get rid of 2-propanol and redissolved in 10 ml toluene and 5 ml $H_2O$. The mixture was stirred for 20 min and layers were separated. The organic layer was dried over $Na_2SO_4$ and concentrated. To the crude product ethyl acetate (10 ml) was added, followed by addition of 0.2 g oxalic acid dissolved in 1 ml EtOH. The suspension was stirred 4 h at ambient temperature and overnight at 5° C. The solid obtained was filtered off and dried at air to give a solid material (0.3 g, 38.5% yield). 98.86% ee purity.

Each of the patents, patent applications, and journal articles mentioned above are incorporated herein by reference. The invention having been described it will be obvious that the same may be varied in many ways and all such modifications are contemplated as being within the scope of the invention as defined by the following claims.

What is claimed is:

1. A process, which comprises:
   a) reacting a compound of formula (1) with a compound of formula (7) in the presence of a base,

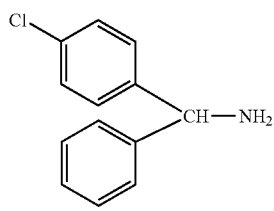

(1)

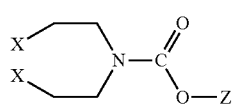

(7)

to form a compound of formula (8):

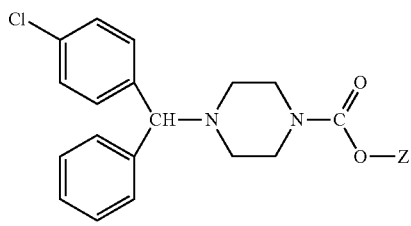

(8)

wherein X is a leaving group reactive with an amine;
Z is a C7-C20 aralkyl group or a C6-C20 aryl/alkylaryl group, each of which groups can be substituted by one to four halogen, alkoxy, amino, and/or nitro groups; and
b) deprotecting said compound of formula (8) to form a compound of formula (4)

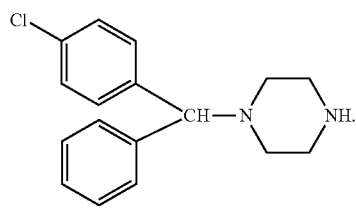

(4)

2. The process according to claim 1, wherein Z is selected from phenyl, p-tolyl, p-methoxyphenyl, and benzyl.

3. The process according to claim 2, wherein Z is phenyl.

4. The process according to claim 1, wherein X is a halo group or a sulphonyl group.

5. The process according to claim 4, wherein X is a group selected from chloro, bromo, mesyloxy, besyloxy, and tosyloxy.

6. The process according to claim 5, wherein X is a chloro group.

7. The process according to claim 1, wherein said compound of formula (7) is N,N-bis(2-chloroethyl)phenyl carbamate of formula (7a)

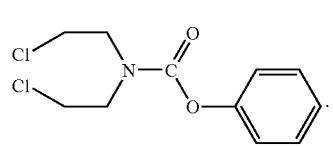

(7a)

8. The process according to claim 1, wherein the compounds of formulae (1), (8), and (4) are racemic compounds.

9. The process according to claim 1, which further comprises converting said compound of formula (4) to a cetirizine compound.

10. The process according to claim 1, wherein the compounds of formulae (1), (8), and (4) are substantially the (R)-enantiomer compounds.

11. The process according to claim 10, wherein said compound of formula (4) has an optical purity of at least 95%.

12. The process according to claim 11, which further comprises converting said compound of formula (4) to a levocetirizine compound.

13. The process according to claim 10, which further comprises converting said compound of formula (4) to a levocetirizine compound.

14. The process according to claim 1, which further comprises isolating said compound of formula (4) as an oxalate salt.

15. The process according to claim 14, which comprises isolating said oxalate salt of the compound of formula (4) in crystalline form.

16. The process according to claim 1 wherein the deprotection is performed without using HBr in acetic acid.

17. The process according to claim 1 wherein the deprotection is performed by an aqueous alkali.

18. The process according to claim 1, wherein the reacting is performed using potassium iodide as an initiator.

19. The process according to claim 1, wherein said compounds of formulas (7) and (8) are compounds of formulas (7a) and (8a), respectively,

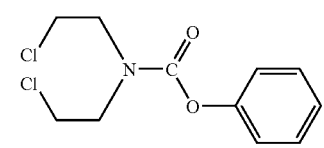

(7a)

-continued

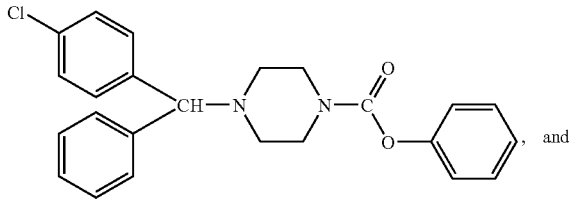
(8a)

, and wherein said base is an organic base.

20. The process according to claim 19, wherein said organic base is diisopropylethylamine.

21. The process according to claim 19, wherein said reacting step (a) proceeds at a temperature between 50° C. and 150° C.

22. The process according to claim 19, wherein said reacting step (a) comprises the presence of potassium iodide as an initiator.

23. The process according to claim 19, which further comprises:
 isolating said compound of formula (4) as an oxalate salt; and
 converting said oxalate salt of the compound of formula (4) into levocetirizine.

* * * * *